United States Patent [19]

Gozzo et al.

[11] 4,195,036

[45] Mar. 25, 1980

[54] DICHLOROACETAMIDES WHICH ARE ANTIDOTES FOR PROTECTING MAIZE AGAINST THE TOXIC ACTION OF HERBICIDAL ESTERS OF N,N-DISUBSTITUTED GLYCINES, METHODS FOR PREPARING THE ANTIDOTES, AND COMPOSITIONS COMPRISING THEM

[75] Inventors: Franco Gozzo, S. Donato Milanese; Luigi Abbruzzese, Milan; Giorgio Siddi, S. Donato Milanese, all of Italy

[73] Assignee: Montedison S.p.A., Milan, Italy

[21] Appl. No.: 846,351

[22] Filed: Oct. 28, 1977

[30] Foreign Application Priority Data

Oct. 29, 1976 [IT] Italy ............................. 28867 A/76

[51] Int. Cl.$^2$ ........................................... C07C 103/27
[52] U.S. Cl. ............................. 260/561 HL; 71/118; 71/111; 260/562 B

[58] Field of Search ................... 260/561 HL, 562 B; 71/118

[56] References Cited

U.S. PATENT DOCUMENTS

| 4,021,224 | 5/1977 | Pallos et al. | 71/118 |
| 4,033,756 | 7/1977 | Hoffmann | 71/118 |

FOREIGN PATENT DOCUMENTS 2402983  8/1974  Fed. Rep. of Germany ............. 71/118

Primary Examiner—Glennon H. Hollrah

[57] ABSTRACT

There are disclosed dichloroacetamides which are antidotes that are particularly and specifically active against the toxic action exerted on maize cultivations by herbicidal esters of N,N-disubstituted glycines; methods for preparing the antidotes, and compositions comprising them, in particular compositions comprising both the antidotes and the herbicidal esters of N,N-disubstituted glycines.

3 Claims, No Drawings

DICHLOROACETAMIDES WHICH ARE ANTIDOTES FOR PROTECTING MAIZE AGAINST THE TOXIC ACTION OF HERBICIDAL ESTERS OF N,N-DISUBSTITUTED GLYCINES, METHODS FOR PREPARING THE ANTIDOTES, AND COMPOSITIONS COMPRISING THEM

THE PRIOR ART

Esters of glycine, substituted at the nitrogen atom, and having herbicidal properties are described in, for instance, U.S. Pat. No. 3,780,090 and German patent application No. 2,311,897.

More particularly, esters of N-(chloroacetyl-)-N-(2,6-dialkylphenyl) glycine of the general formula:

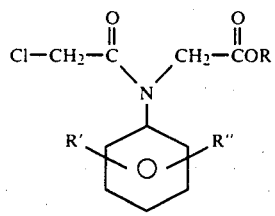

have been found to exert good herbicidal action on maize. However, those herbicides are rather noxious to maize and, therefore, it is not possible to use them in practice in maize cultivation.

French patent application No. 2,133,793 describes herbicidal compositions consisting of a herbicide (thiolcarbamates and substituted triazines being exemplified) and an antidote of the general formula:

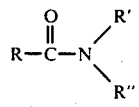

in which R may be, among others, a dichloromethyl group, and R' and R" represent numerous alkylene, alkyl, aryl groups, etc. Such compositions permit the use of the thiolcarbamates and substituted triazines in the disherbing of maize and wheat fields without prejudice to the useful plants.

THE PRESENT INVENTION

One object of this invention is to provide antidotes which exert a detoxicating action on maize, neutralizing the damages caused to maize cultivations by the herbicides of general formula (I).

Another object is to provide compositions comprising antidotes according to this invention and herbicides of formula (I).

These and other objects are accomplished by the present invention which provides antidotes which are dichloroacetamides of the general formula:

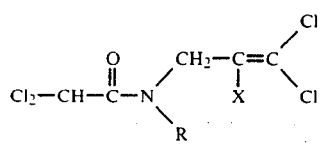

in which
X is H or halogen; and
R is H, alkyl having from 1 to 5 carbon atoms, (poly)-haloalkyl, alkenyl, (poly)-haloalkenyl, alkinyl, (poly)-haloalkinyl all having from 2 to 5 carbon atoms, or phenyl.

Unexpectedly, the detoxicating action on maize of the dichloroacetamides of formula (II) is up to ten times greater than that exerted by N-dialkyl-dichloroacetamide, the most active antidote described in French patent application No. 2,133,793.

The antidoes of this invention which are N-(3,3-dichloro-2-X-alkyl) dichloroacetamides are partly, and generically, comprised in French patent application No. 2,133,793, when, in the general formula

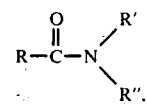

R is haloalkyl, R' is haloalkenyl and R" is haloalkenyl, alkyl, alkenyl, or phenyl. However, said dichloroacetamides are not described as chemical compounds in the French patent application No. 2,133,793. Moreover, no antidote activity with respect to herbicides of general formula (I) for the protection of maize is established in the French patent application, nor is there any suggestion in the latter of the fact that the dichloroacetamides having formula (I) of this invention could have an antidote action decidedly superior to that developed by the compounds described therein.

The dichloroacetamides of formula (II) can be prepared by reacting a N-substituted-N-(3,3- dichloro-2-X-alkyl) amine with dichloroacetyl chloride in the presence of a HCl acceptor which may be an excess of the amine, at room temperature and optionally in an inert solvent, the reaction proceeding as follows:

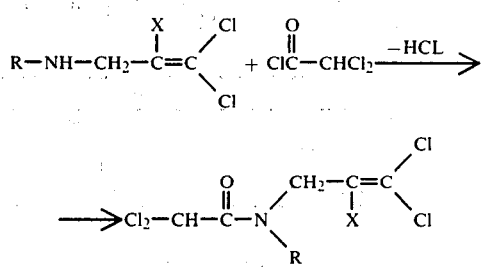

The starting amine is prepared by alkylation of the R-NH₂ amine with 1,3-trichloro-2-X-propene according to the equation:

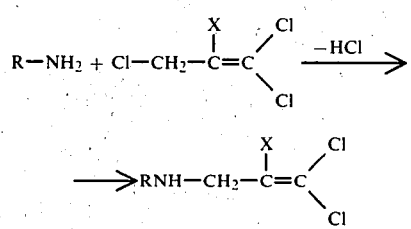

Said reaction is carried out in the presence of a HCl acceptor which may be an excess of the amine and, optionally, in an inert solvent.

The antidotes of the invention are compatible in all proportions (ratios) with the herbicidal compounds of general formula (I). They may be formulated in the presence of diatomite under the usual conditions suitable for obtaining powders, possibly in the presence of surfactants, both alone or in admixture with the compounds of general formula (I).

By methods known to the skilled in the art, the compositions may be formulated as suspension or sprayable aqueous dispersion, in the presence of surfactants and/or solvents.

The activity antidote is perceptible in doses of 0.1 kg/ha in the presence of toxic doses (4hg/ha) of the herbicides of general formula (I).

The following examples are given to illustrate the invention in more detail and are not intended to be limiting.

EXAMPLE 1

To 1.2 moles of allylamine dissolved in 200 ml of benzene, were added dropwise and under stirring at the boiling temperature of the mixture, 0.3 mole of 1,3,3-trichloropropene, diluted with 50 ml of the same solvent.

Once the addition was accomplished, the mixture was maintained at boiling for another 2 hours, after which it was washed with water and then dried.

After removal of the solvent, there remained an oil, N-allyl-N-(3,3-dichloroallyl)amine, which distills under reduced pressure: $b.p._{18mm} = 79° - 81°$ C.

To 0.04 mole of the amine thus obtained, dissolved in 50 ml of dichloroethane, there was added dropwise, under stirring, 0.02 mole of dichloroacetyl chloride, diluted with 20 ml of the same solvent.

After the addition had been accomplished, the mixture was maintained under stirring for a further 2 hours at room temperature. After removal of the solid that had formed (amine hydrochloride), the dried solution was subjected to evaporation. The residue, N-alkyl-(3,3-dichloroallyl) dichloroacetamide, (our Mark M7601) which was a yellowish oil, was distilled under reduced pressure: $b.p._{0.4mm} = 105° - 8°$ C.

| Theor. % | Found % |
|---|---|
| Cl = 51.20 | 50.54 |
| C = 34.69 | 34.31 |
| H = 3.27 | 3.19 |
| N = 5.06 | 5.15 |

EXAMPLE 2

To 2 moles of methylamine (a 33% aqueous solution) was added, dropwise, at room temperature, 0.2 mole of 1,3,3-trichloropropene, dissolved in 120 ml of methanol. When the addition was terminated, the mixture was kept under stirring for another 3 hours and then was allowed to rest overnight.

By extraction of the reaction product with dichloromethane or with ethyl ether, followed by evaporation of the dried substances, there was obtained a yellowish oil, N-methyl-N-(3,3-dichloroallylamine), which was distilled under reduced pressure: $b.p._{15 mm} = 51° - 52°$ C.

By reaction of this amine with dichloroacetyl chloride as in Example 1, N-methyl-N-(3,3-dichloroallyl)-dichloroacetamide (our ref. Mark M 7637), a yellow oil is obtained.

| Theor. % | Found % |
|---|---|
| Cl = 56.51 | Cl = 55.77 |
| C = 28.72 | C = 28.02 |
| H = 2.81 | H = 2.73 |
| N = 5.58 | N = 5.44 |

EXAMPLE 3

To 0.2 mole of hexamethylentetraamine dissolved in 300 ml of ethanol at 50° C. and under stirring, there was added 0.2 mole of NaI, then, dropwise, 0.2 mole of 1,3,3-trichloropropene.

After completion of the addition, the mixture was kept under stirring for another 2 hours and then allowed to stand for 24 hours.

After saturation with gaseous HCl, the mixture was allowed to stand for another 12 hours. After removal of the solid present, by filtration under vacuum, the liquid was evaporated. The residue, the amine hydrochloride, was washed with dichloromethane and then dried. It melted at between 215° and 217° C. The free amine, N-(3,3-dichloroallyl)amine, obtained from the hydrochloride by alkalinization of the aqueous solution and by extraction with ethyl ether, boiled at 53° C. under a pressure of 15 mm. Hg.

By reaction of the N-(3,3-dichloroallyl)amine with the dichloroacetyl chloride, as in Example 1, there was obtained N-(3,3-dichloroallyl)dichloroacetamide.

| Theor. % | Found % |
|---|---|
| Cl = 59.86 | Cl = 58.01 |
| C = 25.35 | C = 25.75 |
| H = 2.13 | H = 2.15 |
| N = 5.91 | N = 6.11. |

EXAMPLES 4 to 7

Using the same process as in Example 2, there was obtained, from methylamine and 1,2,3,3-tetrachloropropene, N-methyl-N-(2,3,3-trichloroallyl)-amine, with $b.p._{15mm} = 67°$ C., and which, by reaction with dichloroacetyl chloride, yielded N-methyl-N-(2,3,3-trichloroallyl)-dichloroacetamide (Applicants' Mark M 8069), a yellow oil.

| Theor. % | Found % |
|---|---|
| Cl = 62.12 | Cl = 60.20 |
| C = 25.25 | C = 25.06 |
| H = 2.12 | H = 2.11 |
| N = 4.91 | N = 5.04. |

From ethylamine and 1,2,3,3-tetrachloropropene, proceeding as in Example 1, there was obtained N-ethyl-N-(2,3,3-trichloroallyl)-amine with $b.p._{35 mm} = 91°$ C.-92° C.

From said product, by reaction with dichloroacetyl chloride, there was obtained N-ethyl-N-(2,3,3-trichloroallyl)dichloroacetamide, (Applicants' Mark M 8280), as a yellow oil. The elementary percentual analysis gave:

| Theor. % | Found % |
|---|---|
| Cl = 59.21 | Cl = 58.74 |
| C = 28.08 | C = 28.09 |
| H = 2.69 | H = 2.72 |

-continued

| Theor. % | Found % |
|---|---|
| N = 4.67 | N = 4.40 |

By proceeding as in Example 1, from isopropylamine and 1,2,3,3-tetrachloropropene there was prepared N-isopropyl-N-2,3,3-trichloroallyl)-amine: b.p.$_{18\ mm}$=84°-85° C.

By reaction thereof with dichloroacetyl-chloride there was obtained N-isopropyl-N-(3,3,2-trichloroallyl)-dichloroacetamide (Applicants' Mark M 8281) having a melting point=51°-52° C. (crystallized by n-hexane).

| Theor. % | Found % |
|---|---|
| Cl = 56.56 | Cl = 55.38 |
| C = 30.66 | C = 30.77 |
| H = 3.21 | H = 3.17 |
| N = 4.47 | N = 4.00. |

From propargylamine and 1,3,3-trichloropropene, proceeding as in Example 1, there was prepared N-propargyl-N-(3,3-dichloroallyl) amine: b.p.$_{15\ mm}$=88°-91° C., from which, by reaction with dichloroacetyl chloride, there was obtained N-propargyl-N-(3,3-dichloroallyl)dichloroacetamide, (Applicants' Mark 8341), a yellowish oil.

| Theor. % | Found % |
|---|---|
| Cl = 51.57 | Cl = 50.52 |
| C = 34.94 | C = 34.81 |
| H = 2.56 | H = 2.67 |
| N = 5.09 | N = 4.81. |

EXAMPLE 8

To a series of pots with an upper diameter of 10 cm and a height of 10 cm, filled with sandy soil and in each of which there had been sown a certain infesting grass (see Table infra.) and maize, there was added water in the amount necessary for a good germination or sprouting of the seeds. Immediately thereafter a series of said pots was treated with the herbicide N-(2-methyl-6-ethyl-phenyl)-N-(isopropyl-carboxylmethyl)-chloroacetamide, (Applicants' Mark HS 26910; see formula I in which R is isopropyl, R' is methyl, and R" is ethyl) in the form of a hydroacetonic dispersion (20% vol/vol) in doses of 4 kg/ha of active principle by application on the surface of the soil, following by covering with an additional layer of 0.5 cm of soil.

A second series of pots was treated, with the same dose and under the same conditions, with the herbicide N-(2,6-diethylphenyl)-N-(ethylcarboxymethyl)-chloroacetamide ("Antor", Hercules); see formula I in which R is ethyl and R' and R" are ethyl.

A third and fourth series of pots were treated, under the same conditions, with a hydroacetonic dispersion containing, respectively, the herbicide HS 26910 and herbicide "Antor", to each of which was added antidotes M7601 and, separately, M8069, in different proportions so as to obtain, in each instance, a dose of 4 kg/ha of herbicide together with a dose of from 0.1 to 0.8 kg/ha of one or the other of the antidotes of the invention.

For comparative purposes, a further two series of pots were treated under the same conditions with two hydroacetonic dispersions containing, respectively, herbicide HS 26910 and herbicide "Antor", each of which had been additioned with antidote N-diallyl-dichloroacetamide (Mark R 25788; Stauffer) in the same proportions as those applied with the two antidotes M7601 and M8069.

A seventh series of pots, in which only maize had been sown, was treated with a hydroacetonic dispersion of antidotes M7601 and M8069 only in doses varying from 0.1 to 0.8 Kg/ha. This application has no negative effect on the maize plants.

Finally, a last series of pots not treated with any foreign substance, was kept as control.

All the series of pots were kept under observation in an environment conditioned at temperatures comprised between 15° C. and 24° C., with a relative humidity of 70%, a photoperiod of 12 hours and a light intensity of 2.500 lux.

Every two days all the pots were uniformly watered so as to ensure a degree of humidity sufficient for a good development of the plants.

After 14 (and 21) days from the treatment, observations on the vegetative state of the plants were made using evaluations expressed on the basis of a value scale ranging from 0 (=growth equal to that of the control plants) to 4 (=complete stop of the growth).

In the Table which follows there are recorded the results obtained under each of the indicated conditions and for each plant studied.

As appears clearly from the Table:
(1) both tested herbicides proved to be phytotoxic with respect to maize, showing a degree of toxicity at about 3 at the dosage of 4 Kg/ha.;
(2) the application of either one of the two herbicides HS 26910 and "Antor" in a dose of 4 Kg/ha in combination with either the one or the other of the two substances M7601 and M8069, in doses of from 0.2 to 0.8 Kg/ha, eliminates completely the damage caused to the maize by the two herbicides applied singly, without however, reducing the herbicide activity against the infesting plants;
(3) the damage caused to the maize by the application of either the one or the other of the two herbicides, HS 26910 and "Antor", at a dose of 4 Kg/ha, is attenuated in a proportional way by the addition of increasing doses of antidote R-25788, without, however, being completely eliminated even at the dose of 0.8 Kg/ha.

TABLE

Herbicide activity of the N-di-substituted glycines on infesting plants and on maize, in comparison with the activity in the presence of antidotes according to the invention and according to the French Patent Application No. 2,133,793.

| Substances applied | Dose Kg/ha | Infesting plants* at 21 days from treatment | | | | | | | | Maize 14 days from treatment | 21 days from treatment |
|---|---|---|---|---|---|---|---|---|---|---|---|
| | | E. | A. | L. | SO. | SE. | V. | R. | G. | | |
| HS 26910 | 4 | 4 | 4 | 4 | 4 | 4 | 4 | 4 | 4 | 3 | 3 |
| HS 26910 + M 7601 | 4 + 0.1 | | | | " | | | | | 1 | 1 |

TABLE-continued

Herbicide activity of the N-di-substituted glycines on infesting plants and on maize, in comparison with the activity in the presence of antidotes according to the invention and according to the French Patent Application No. 2.133.793.

| Substances applied | Dose Kg/ha | Infesting plants* at 21 days from treatment | | | | | | | | Maize 14 days from treatment | 21 days from treatment |
|---|---|---|---|---|---|---|---|---|---|---|---|
| | | E. | A. | L. | SO. | SE. | V. | R. | G. | | |
| HS 26910 + M 7601 | 4 + 0.2 | | | | '' | | | | | 0 | 0 |
| HS 26910 + M 7601 | 4 + 0.4 | | | | '' | | | | | 0 | 0 |
| HS 26910 + M 7601 | 4 + 0.8 | | | | '' | | | | | 0 | 0 |
| HS 26910 + M 8069 | 4 + 0.1 | | | | '' | | | | | 2 | 2 |
| HS 26910 + M 8069 | 4 + 0.2 | | | | '' | | | | | 1 | 1 |
| HS 26910 + M 8069 | 4 + 0.4 | | | | '' | | | | | 1 | 1 |
| HS 26910 + M 8069 | 4 + 0.8 | | | | '' | | | | | 0 | 0 |
| HS 26910 + R 25788 | 4 + 0.1 | | | | '' | | | | | 2.5 | 2.5 |
| HS 26910 + R 25788 | 4 + 0.2 | | | | '' | | | | | 2 | 2 |
| HS 26910 + R 25788 | 4 + 0.4 | | | | '' | | | | | 1 | 1 |
| HS 26910 + R 25788 | 4 + 0.8 | | | | '' | | | | | 1 | 1 |
| Antor | 4 | | | | '' | | | | | 3 | 3 |
| Antor + M 7601 | 4 + 0.1 | | | | '' | | | | | 1 | 1 |
| Antor + M 7601 | 4 + 0.2 | | | | '' | | | | | 0 | 0 |
| Antor + M 7601 | 4 + 0.4 | | | | '' | | | | | 0 | 0 |
| Antor + M 7601 | 4 + 0.8 | | | | '' | | | | | 0 | 0 |
| Antor + M 8069 | 4 + 0.1 | | | | '' | | | | | 2 | 2 |
| Antor + M 8069 | 4 + 0.2 | | | | '' | | | | | 1 | 1 |
| Antor + M 8069 | 4 + 0.4 | | | | '' | | | | | 1 | 1 |
| Antor + R 25788 | 4 + 0.1 | | | | '' | | | | | 2.5 | 2.5 |
| Antor + R 25788 | 4 + 0.2 | | | | '' | | | | | 1.5 | 2 |
| Antor + R 25788 | 4 + 0.4 | | | | '' | | | | | 1 | 1.5 |

*E. = Echinochloa crusgalli;
A. = Avena fatua;
L. = Lolium italicum;
SO. = Sorghum spp.;
SE. = Setaria glauca;
V. = Vigna sinensis;
R. = Rumex crispus;
G. = Galinsoga parviflora.

We claim:
1. A dichloroacetamide having the general formula

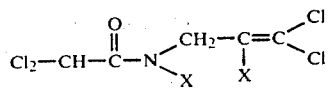

in which

X is H or chlorine; and
R is H, an alkyl having from 1 to 5 carbon atoms, or an alkenyl having from 2 to 5 carbon atoms.

2. Acetamide according to claim 1, characterized in that said acetamide is N-allyl-N-(3,3-dichloroallyl)-dichloroacetamide.

3. Acetamide according to claim 1, characterized in that said acetamide is N-methyl-N-(2,3,3-trichloroallyl)-dichloroacetamide.

* * * * *

UNITED STATES PATENT OFFICE
CERTIFICATE OF CORRECTION

Patent No. 4,195,036           Dated March 25, 1980

Inventor(s) Franco GOZZO et al

It is certified that error appears in the above-identified patent and that said Letters Patent are hereby corrected as shown below:

In Claim 1, the structural formula should read as follows:

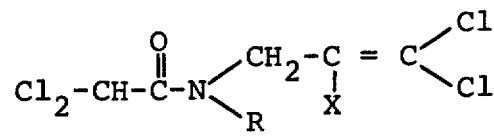

Signed and Sealed this

*Twenty-fourth* Day of *June 1980*

[SEAL]

*Attest:*

SIDNEY A. DIAMOND

*Attesting Officer*     *Commissioner of Patents and Trademarks*